United States Patent [19]

Lutze et al.

[11] Patent Number: 5,035,232
[45] Date of Patent: Jul. 30, 1991

[54] RETRACTOR

[75] Inventors: Theodor Lutze, Balgheim; Dieter Weisshaupt, Immendingen, both of Fed. Rep. of Germany

[73] Assignee: Aesculap AG, Fed. Rep. of Germany

[21] Appl. No.: 469,577

[22] PCT Filed: Oct. 21, 1988

[86] PCT No.: PCT/EP88/00945

§ 371 Date: Mar. 30, 1990

§ 102(e) Date: Mar. 30, 1990

[87] PCT Pub. No.: WO89/03660

PCT Pub. Date: May 5, 1989

[30] Foreign Application Priority Data

Oct. 24, 1987 [DE] Fed. Rep. of Germany ....... 3736066

[51] Int. Cl.$^5$ ............................................ A61B 17/02
[52] U.S. Cl. ........................................ 128/20; 128/11
[58] Field of Search ................. 128/20, 11, 16, 18, 128/6, 23; 362/119, 120; 350/96.4, 96.5, 96.2, 96.3, 96.6

[56] References Cited

U.S. PATENT DOCUMENTS

| | | | |
|---|---|---|---|
| 3,195,536 | 7/1965 | Hovnanian et al. | 128/6 |
| 3,592,199 | 2/1971 | Ostensen | 128/23 |
| 3,986,854 | 10/1976 | Scrivo et al. | 128/11 |
| 4,562,832 | 1/1986 | Wilder et al. | 128/20 |
| 4,570,614 | 2/1986 | Bauman | 128/11 |
| 4,597,030 | 6/1986 | Brody et al. | 128/20 |

FOREIGN PATENT DOCUMENTS

| | | | |
|---|---|---|---|
| 101781 | 3/1984 | European Pat. Off. | 128/20 |
| 2359085 | 6/1974 | Fed. Rep. of Germany | 128/20 |
| 3023266 | 7/1982 | Fed. Rep. of Germany | 128/20 |
| 3301890 | 8/1984 | Fed. Rep. of Germany | 128/20 |

OTHER PUBLICATIONS

"Fiberoptics for Surgery", Applied Fiberoptics, Inc., No. 0219/81.

Primary Examiner—Edward M. Coven
Assistant Examiner—M. Graham
Attorney, Agent, or Firm—Barry R. Lipsitz

[57] ABSTRACT

In a retractor with a retractor blade, a handle, a fiber-optical light guide for illuminating the point of engagement of the retractor and a connector for connecting a fiber-optical cable to the fiber-optical light guide, with the fiber-optical light guide comprising a bent, tubular sheath which extends through the handle and along part of the retractor blade and in which a glass fiber bundle is embedded, in order to improve resterilizability, with the retractor being at the same time capable of being disassembled, a sheath that comprises fixing elements for detachably securing the retractor blade on the sheath, and the handle being positioned loosely on the rear end of the sheath and fixed in this position by a detachable holding element.

14 Claims, 2 Drawing Sheets

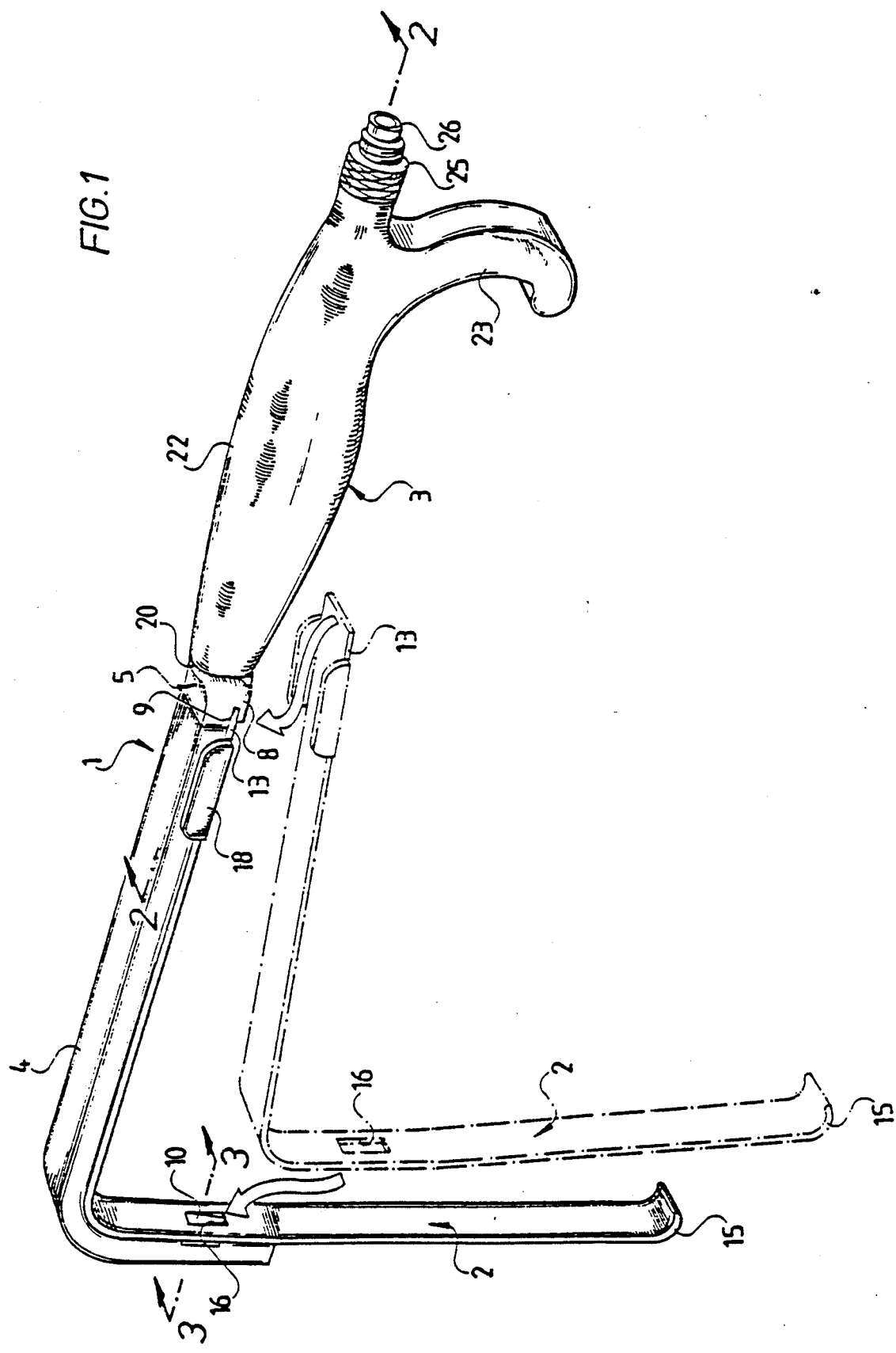

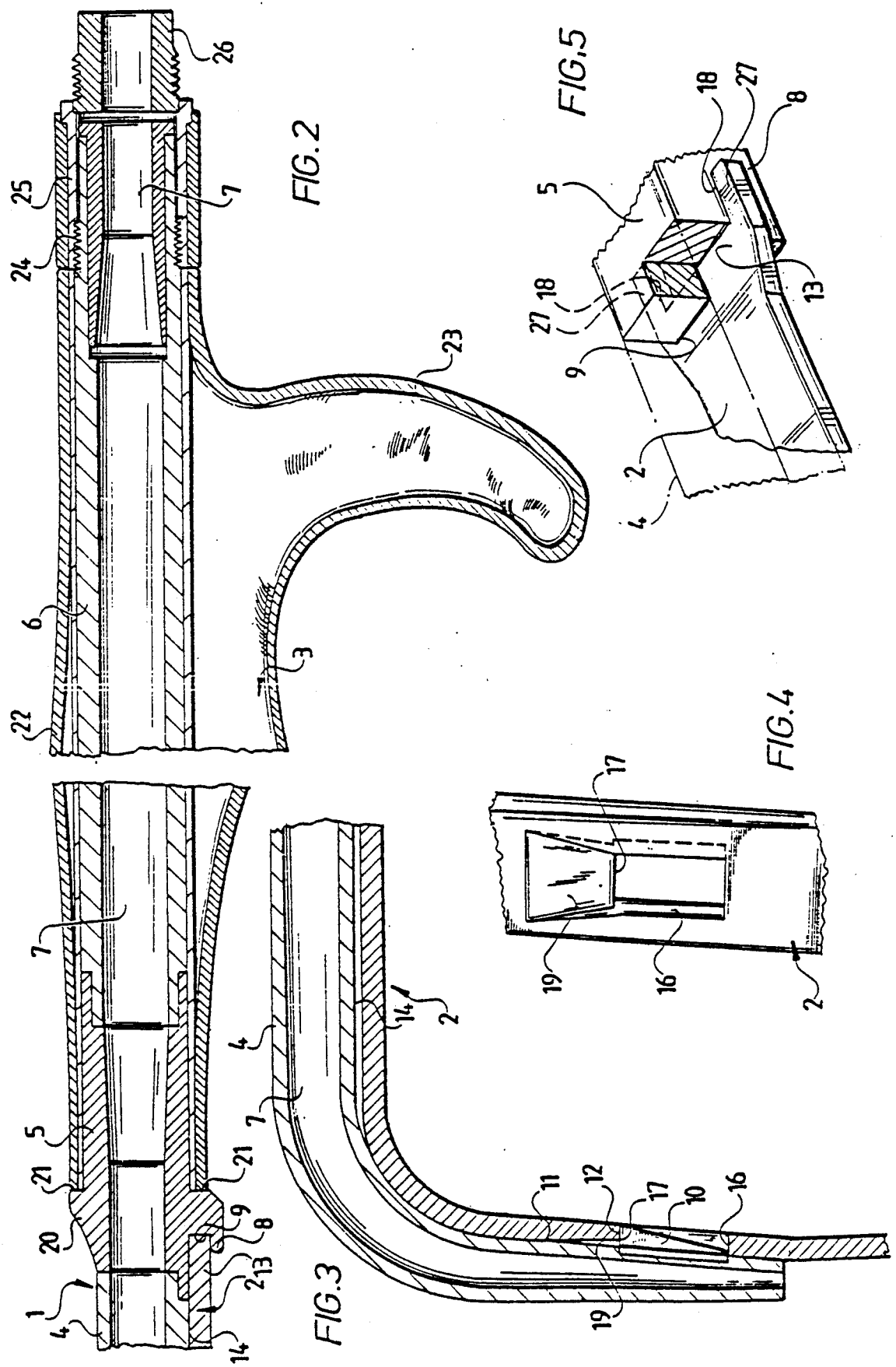

RETRACTOR

BACKGROUND OF THE INVENTION

The invention relates to a retractor with a retractor blade, a handle, a fiber-optical light guide for illuminating the point of engagement of the retractor and a connector for connecting a fiber-optical cable to the fiber-optical light guide, with the fiber-optical light guide comprising a bent, tubular sheath which extends through the handle and along part of the retractor blade and in which a glass fiber bundle is embedded.

Retractors are known wherein a plastic retractor blade is directly connected to a fiber-optical light guide so that light is conducted through the plastic blade to the front edge at which it exits (EP-B1 101 781). Such an instrument is normally used as a disposable, plastic product which is not resterilizable. In other known instruments of this kind, the handle can be used again, but the plastic blades are designed as disposable parts (DE-OS 33 01 890).

In other known retractors, a handle through which there extends a tube accommodating a fiber bundle is formed directly on the retractors. This tube is firmly soldered or welded to the metallic retractor (company prospectus "Fiberoptics for Surgery" Applied Fiberoptics, Inc., 0219/81, pages 5 et seq. ). The tube mounted on the blade can cause limited vision, and, in addition, the soldered joints produce corners and edges which make proper cleaning from a hygienic point of view difficult.

SUMMARY OF THE INVENTION

The object of the invention is to so improve a retractor of the kind described at the begining that all parts of the instrument are resterilizable and that simple disassembly of the instrument into its individual parts for sterilization purposes is possible.

This object is accomplished in accordance with the invention in a retractor of the kind described at the beginning in that the sheath comprises fixing elements for detachably securing the retractor blade on the sheath, and in that the handle is positioned loosely on the rear end of the sheath and fixed in this position by a detachable holding element. Hence the sheath accommodating the bundle of optical fibers forms a support for the retractor having secured thereon, on the one hand, detachably the retractor blade and, on the other hand, by simple positioning thereon, a handle part which is detachably fixable on the sheath. The parts can be taken apart in a simple way, and all the individual parts can then be cleaned and resterilized in a simple manner, with none of the parts having recesses or edges to raise cleaning or sterilizing problems.

A particularly secure positioning of the retractor blade is obtained when the sheath has a plane contact surface for the retractor blade.

The sheath is preferably of rectangular cross-section, at least in the part in which the retractor blade rests against. It is advantageous for the glass fibers to be adhesively bonded to one another and to the sheath at least at both ends of the sheath. This results in a completely sealed sheath construction so that the sheath component can be sterilized as often as required without any fear of damage to the sensitive glass fibers.

In the preferred embodiment, provision is made for the sheath to have a notch or groove extending transversely to its longitudinal direction to accommodate the end of the retractor blade near the handle and for a detent element to be arranged at the front end of the sheath to make a releasable detent connection with a complementary detent element on the retractor blade. This enables attachment of the retractor blade to the sheath and removal from it again in a very simple way, and yet during actuation it is held firmly on the sheath so that, in all, even large forces can be transmitted with the instrument. If necessary, it is thus possible to exchange the retractor blade quickly so the same retractor can be used successively with retractor blades of the desired dimensions.

It is particularly advantageous for the detent element on the sheath to be wedge-shaped projection having at the top a supporting surface extending transversely to the plane of the retractor blade, and for a recess to be arranged in the retractor blade as complementary detent element. Provision is preferably made for an inclined depression to adjoin the top edge of the recess in the retractor blade on the side facing the sheath. This enables the retractor blade to snap in elastically when inserted, with the retractor blade thereby becoming, in all, elastically deformed to a slight extend. When it has snapped in, the retractor blade sits in a positively and frictionally connected manner on the sheath; for removal, the free end of the retractor blade has to be bent elastically in the direction of the handle in order to release the detent connection again.

The groove or notch for accommodating the end of the retractor blade near the handle can be arranged in a thicker portion of the sheath which preferably simultaneously forms a front stop for the handle.

Furthermore, provision may be made for the retractor blade to comprise on its end near the handle guiding surfaces which rest against both sides of the sheath when the retractor blade is inserted. In this way, on the one hand, insertion of the retractor blade is facilitated, and, on the other hand, these lateral guiding surfaces secure the retractor blade on the sheath against lateral displacement.

In the further preferred embodiment, provision is made for a coupling ring to be screwable onto the end of the sheath protruding from the handle when the latter is positioned thereon to enable connection with the fiber-optical cable. Hence this acts as a quick closure device between the fiber-optical cable and the sheath accommodating the optical fibers.

It is particularly advantageous for the screwed-on coupling ring to rest against the handle and press it against a front stop. The coupling ring providing the quick connection then serves simultaneously to axially fix the handle on the sheath so that, conversely, after release of the connection, the handle can be readily exchanged.

It is particularly advantageous for the retractor blade to be band-shaped or strip-shaped in the area of contact with the sheath. It then fixes itself over the entire length on the sheath, with extremely effective stabilization thereby being imparted to it. On the other hand, this design permits elastic deformation to a slight extend so that insertion and removal of the retractor blade are thereby made possible.

BRIEF DESCRIPTION OF THE DRAWINGS

The following description of preferred embodiments serves in conjunction with the drawings to explain the invention in further detail. The drawings show:

FIG. 1 a perspective view of a retractor with the retractor blade inserted (continous lines) and with the retractor blade removed (dot-and-dash lines);

FIG. 2 a sectional view along line 2—2 in FIG. 1;

FIG. 3 a sectional view along line 3—3 in FIG. 1;

FIG. 4 a plan view of the recess in the retractor blade seen from the sheath side; and FIG. 5 the end region of a modified embodiment of a retractor blade with laterally protruding prongs.

DETAILED DESCRIPTION OF THE INVENTION

The retractor illustrated in FIG. 1 comprises essentially three parts, namely a tubular, metallic housing of rectangular cross-section which is bent at a right angle at one end and is designated sheath 1 in the following, a generally L-shaped retractor blade 2 made of band-shaped or strip-shaped metal which is detachably connected to the sheath 1, and a hollow handle 3 which is positionable on the sheath 1.

In the illustrated embodiment, the sheath itself is comprised of three sections, namely a front section 4 on the retractor side, a middle section 5 and a handle section 6 which is normally arranged inside the handle 3. The three sections of the sheath have a continuous channel 7 of rectangular cross-section which extends on one level through them and may taper in cross-section at its end near the retractor blade (FIG. 3). A plurality of glass fibers—not illustrated in the drawings—are embedded inside this channel. At least at the two ends of the sheath 1, the glass fibers are compactly adhesively bonded to one another and to the inside wall of the sheath 1 so that the channel 7 is completely sealed off to the outside and the fibers are fixed in the sheath and secured against damage. The middle section 5 has at its bottom end a holding projection 8 which forms a notch or groove 9 extending transversely to the longitudinal direction of the sheath 1 and immediately adjoining the plane underside of the sheath 1. The notch or groove 9 is open towards the front end of the retractor. In the proximity of the front end there is arranged on the side of the sheath 1 facing the handle 3 a wedge-shaped detent projection 10 which terminates at the top in a supporting surface 12 extending perpendicularly to the circumferential surface 11.

With their end 13 near the handle, the retractor blades 2 can be pushed into the groove 9. The retractor blades 2 are first positioned at a distance from the underside 14 of the sheath 1 and from the circumferential surface 11. By pressing the free end 15 of the retractor blade 2 which is bent in the direction of the handle, the retractor blade 2 can be swivelled in the direction towards the underside 14 and the circumferential surface 11, with the groove 9 defining the axis of rotation. The one leg of the retractor blade 2 then slides along the wedge-shaped detent projection 10 and is elastically bent away from the circumferential surface 11 until the detent projection 10 snaps into a rectangular detent recess 16 in the retractor blade 2. The detent recess 16 is arranged such that the top edge 17 of the detent recess 16 rests on the supporting surface 12 and thereby brings the retractor blade 2 into contact with both the underside 14 and the circumferential surface 11 of the sheath 11. In this attached position, illustrated in continuous lines in FIG. 1, the retractor blade 2 is fixed on the sheath 1 so that forces can be transmitted from the sheath 1 onto the retractor blade 2. This fixing is furthered by lateral lugs or guiding surfaces 18 which are located at the end of the retractor blade 12 near the handle and rest against the side surfaces of the sheath 1.

The snapping-in of the retractor blade 2 is facilitated by an inclined depression 19 (FIG. 3) adjoining the top edge 17 of the detent recess 16 on the side facing the sheath 1 so that the thickness of the material of the retractor blade 2 in the region of the top edge 17 is less than at other points. The retractor blade 2 can thereby slide more easily along the detent projection 10 while being attached.

Although the retractor blade 2 is fixed on the sheath 1 in such a way that even considerable forces can be transmitted, it can be detached from the sheath 1 againg in a simple manner by the retractor blade 2 being bent at the free end 15 in the direction towards the handle 3. It is thereby possible to swivel the retractor blade 2 about the axis of rotation formed by the groove 9 in the counterclockwise direction (FIG. 1) past the detent projection 10 so that the retractor blade 2 can be subsequently pulled out of the groove 9. In this way, it is possible to change the retractor blade 2 at any time.

The holding projection 8 and a thicker portion 20 on the top of the middle section 5 together form an axial stop surface 21 for the handle 3 which is pushed onto the sheath 1 from the rear side. This handle 3 itself has a substantially tubular housing 22 with an anatomically shaped hook 23 formed on its underside. The handle 3 is, in all, somewhat shorter than the handle section 6 of the sheath 1 so that the sheath 1 protrudes from the handle 3 on the rear side. In this region, the sheath 1 carries an external thread 24 onto which a coupling nut 25 of a fiber-optical cable 26 can be screwed such that the end faces of the fiber-optical cable 26 and the sheath 1 lie tight against one another (FIG. 1). Also, the coupling nut 25 thereby fixes itself onto the handle 3 and presses it in the axial direction against the contact surface 21 so that the handle 3 is fixed on the sheath 1 in the axial direction by the coupling nut 25. Owing to the rectangular cross-section of the sheath 1, the handle 3 is secured against rotation.

Hence the sheath 1 accommodating the glass fibers forms the main part of the entire instrument on which retractor blade, handle and fiber-optical cable can be detachably fixed. These parts are easily removed and exchanged, in particular for sterilization, but also for exchange of the retractor blade while surgery is being performed. In the embodiment illustrated in the drawings, the end at which the light emerges from the sheath 1 is in the top third of the vertically bent leg of the retractor blade 2. In principle, this end could assume a different position along this leg.

In the embodiment shown in FIG. 5, the lugs or guiding surfaces 18 are replaced by prongs 27 protruding rearwardly beyond the end of the retractor blade 2. The prongs 27 embrace the holding projection 8 laterally and hence secure the retractor blade 2 against lateral displacement. The inside surfaces of the prongs 27 form the guiding surfaces 18; these guiding surfaces 18 may diverge slightly towards the free end of the prongs 27 so that a centering effect occurs when the retractor blade is inserted.

We claim:

1. Retractor with a retractor blade, a handle, a fiber-optical light guide for illuminating a point of engagement of said retractor and a connector for connecting a fiber-optical cable to said fiber-optical light guide, said fiber-optical light guide comprising a bent, tubular sheath having a rear end which extends through said handle and in which a glass fiber bundle is embedded, wherein a front portion of said sheath extends from said handle to support said retractor blade and comprises fixing elements for detachably securing said retractor blade on said sheath, and wherein said handle is positioned loosely on the rear end of said sheath and fixed in this positioned by a detachable holding element.

2. Retractor according to claim 1, wherein said sheath has a plane contact surface for said retractor blade.

3. Retractor according to claim 1, wherein a portion of said sheath against which said retractor blade rests is of rectangular cross-section.

4. Retractor according to claim 1, wherein the glass fibers in said bundle are adhesively bonded to one another and to at least a portion of said sheath.

5. Retractor according to claim 1, wherein said sheath has a notch or groove extending transversely to its longitudinal direction for receiving an end of said retractor blade near said handle, and wherein a detent element is arranged at a front end of said sheath and forms a releasable detent connection with a complementary detent element on said retractor blade.

6. Retractor according to claim 5, wherein said detent element on said sheath is a wedge-shaped projection having a supporting surface at a top thereof extending transversely to a plane of said retractor blade, and wherein a recess is arranged in said retractor blade as a complementary detent element.

7. Retractor according to claim 6, wherein an inclined depression adjoins a top edge of said recess in said retractor blade on a side facing said sheath.

8. Retractor according to claim 5, wherein said groove or notch is arranged in a relatively thick portion of said sheath.

9. Retractor according to claim 8, wherein said relatively thick portion forms a front stop for said handle.

10. Retractor according to claim 1, wherein said retractor blade has guiding surfaces which rest against sides of said sheath in the vicinity of said handle.

11. Retractor according to claim 1, wherein said connector comprises a coupling ring screwed onto a portion of said sheath protruding from said handle when the latter is positioned thereon to enable connection with said fiber-optical cable.

12. Retractor according to claim 11, wherein said coupling ring rests against said handle and presses the handle against a front stop of said sheath.

13. Retractor according to claim 1, wherein said retractor blade is of band-shaped or strip design in an area of contact with said sheath.

14. Retractor according to claim 10, wherein said guiding surfaces are formed by opposite inside surfaces of prongs which protrude at an end of said retractor blade and laterally embrace a groove or notch of said sheath.

* * * * *